United States Patent
Hansenne et al.

(12) 
(10) Patent No.: US 6,174,517 B1
(45) Date of Patent: Jan. 16, 2001

(54) COMPOSITIONS CONTAINING A DIBENZOYLMETHANE DERIVATIVE AND A TITANIUM OXIDE NANOPIGMENT, AND USES

(75) Inventors: Isabelle Hansenne; Victoria Van Leeuwen, both of Paris (FR)

(73) Assignee: Societe L'Oreal S.A., Paris (FR)

( * ) Notice: Under 35 U.S.C. 154(b), the term of this patent shall be extended for 0 days.

(21) Appl. No.: 08/975,162

(22) Filed: Nov. 20, 1997

Related U.S. Application Data

(63) Continuation of application No. 08/664,425, filed on Jun. 17, 1996.

(30) Foreign Application Priority Data

Jun. 16, 1995 (FR) .................................... 95-07246

(51) Int. Cl.$^7$ ............... A61K 7/42; A61K 7/06; A61K 7/08; A61K 7/00
(52) U.S. Cl. .......... 424/59; 424/70.1; 424/70.9; 424/70.19; 424/70.21; 424/70.24; 424/400; 424/401
(58) Field of Search .................. 424/59, 70.19, 424/70.21, 70.24, 400, 401

(56) References Cited

U.S. PATENT DOCUMENTS 5,306,485 * 4/1994 Robinson ................ 424/59
5,538,716 * 7/1996 Forrestier et al. .......... 424/59

FOREIGN PATENT DOCUMENTS

| 4303983 A1 | 8/1994 | (DE) . |
| 0303995 | 2/1989 | (EP) . |
| 2184356 | 6/1987 | (GB) . |
| 61-215314 | 9/1986 | (JP) . |
| 61-257915 | 11/1986 | (JP) . |
| WO94/04131 | 3/1994 | (WO) . |
| WO 94/17780 | 8/1994 | (WO) . |
| WO 95/17160 | 6/1995 | (WO) . |

OTHER PUBLICATIONS

Kawamura et al; Pigment used for forming UV–intercepting protective film having excellent discoloration preventing effect; AN 95–062326 ABS, Mar. 1995.*

* cited by examiner

*Primary Examiner*—Shelley A. Dodson
(74) *Attorney, Agent, or Firm*—Burns, Doane, Swecker & Mathis, L.L.P.

(57) ABSTRACT

The present invention relates to new cosmetic compositions for topical use which are intended more particularly for the photoprotection of the skin and/or hair against ultraviolet radiation and to their use in the abovementioned cosmetic application. Still more precisely, it relates to antisun compositions which comprise, in a cosmetically acceptable vehicle, an association of a specific screening agent, chosen from dibenzoylmethane derivatives, with at least one inorganic titanium oxide nanopigment treated with silanes and/or silicones.

34 Claims, No Drawings

US 6,174,517 B1

COMPOSITIONS CONTAINING A DIBENZOYLMETHANE DERIVATIVE AND A TITANIUM OXIDE NANOPIGMENT, AND USES

This application is a continuation of application Ser. No. 08/664,425, filed Jun. 17, 1996.

BACKGROUND OF THE INVENTION

Technical Field of the Invention

The present invention relates to new cosmetic compositions for topical use which are intended more particularly for the photoprotection of the skin and/or hair against ultraviolet radiation (these compositions will be called below, more simply, antisun compositions) and to their use in the above-mentioned cosmetic application. Still more precisely, it relates to antisun compositions which comprise, in a cosmetically acceptable vehicle, an association of a specific screening agent, chosen from dibenzoylmethane derivatives, with at least one inorganic titanium oxide nanopigment treated with silanes and/or silicones.

It is known that luminous radiation with wavelengths of between 280 nm and 400 nm allows the human skin to tan, and that rays with wavelengths of between 280 nm and 320 nm, known by the term UV-B, cause erythemas and skin burns which may damage the development of the natural tan; this UV-B radiation must therefore be screened out.

It is also known that UV-A rays, with wavelengths of between 320 nm and 400 nm, which cause the skin to tan, are capable of harming the latter, especially in the case of sensitive skin or skin which is continually exposed to solar radiation. In particular, UV-A rays cause a loss of skin elasticity and the appearance of wrinkles, leading to premature ageing. They promote the triggering of the erythemal reaction or accentuate this reaction in certain individuals and can even be the cause of phototoxic or photoallergic reactions. It is therefore desirable to screen out the UV-A radiation as well.

Numerous organic sunscreens capable of absorbing, with greater or lesser selectivity, the harmful UV-A rays have been proposed to date in the field of cosmetology.

In this context, a particularly advantageous class of UV-A screening agents currently consists of dibenzoylmethane derivatives, and especially 4-methoxy-4'-tert-butyldibenzoylmethane, which in fact exhibit a high intrinsic adsorption capacity. These dibenzoylmethane derivatives, which are now products which are well known per se as UV-A-active screening agents, are described in particular in the French Patent Applications FR-A-2 326 405 and FR-A-2 440 933 and in the European Patent Application EP-A-0 114 607; 4-methoxy-4'-tert-butyldibenzoylmethane, moreover, is currently offered for sale under the trade name "PARSOL 1789" by the company Givaudan.

In order to obtain total protection over the entire solar spectrum in the UV range, it is possible to combine with these dibenzoylmethane derivatives a UV-B screening agent.

Moreover, it is known that the addition of an inorganic pigment, and especially a titanium oxide ($TiO_2$) pigment, makes it possible to increase the photoprotective properties of the sunscreen compositions comprising UV screening agents.

Consequently, the combination of dibenzoylmethane derivatives and $TiO_2$ (nano)pigments is of great interest in the field of antisun compositions.

However, it is found that the combinations of dibenzoylmethane derivatives with inorganic (nano)pigments, and still more especially the combination 4-methoxy-4'-tert-butyldibenzoylmethane/$TiO_2$, have a disadvantage which affects not only the character, and therefore the quality, of the products comprising them, but also their attractiveness to consumers; in effect, for compositions containing this type of combination, a colour change is observed which is manifested in a more or less intense yellowing of the formulas. Apart from the fact that this phenomenon reduces the photoprotective power of the dibenzoylmethane derivatives, and in particular of 4-methoxy-4'-tert-butyldibenzoylmethane, this yellowing is obviously undesirable from a cosmetic viewpoint.

It is observed, moreover, that this phenomenon is particularly marked in the case of $TiO_2$ nanopigments.

In order to solve this problem, certain solutions have already been proposed in the prior art; thus, in Japanese Patent Application JP 61-215314, the use of sequestrants chosen from edetic, metaphosphoric and polyphosphoric acids and/or their salts was recommended in order to reduce this phenomenon of yellowing. However, this solution does not give complete satisfaction.

Now, following major studies carried out in the field of photoprotection set out above, the Applicant has discovered that the use of titanium oxide (nano)pigments treated with a silicone (siloxane or silane derivative) significantly reduced the yellowing which is commonly observed in the antisun compositions containing conventional combinations of the dibenzoylmethane derivative/$TiO_2$ pigment type.

It is this discovery which forms the basis of the present invention.

It should be noted here that, from the document WO-A-94 04131, photostable screening compositions are known which comprise, in well-defined proportions, a dibenzoylmethane derivative in combination with a benzylidenecamphor derivative. According to this document, the benzylidenecamphor, in the proportions indicated, makes it possible to stabilize the dibenzoylmethane derivative to light, in other words to limit its degradation under the action of UV rays, especially UV-A rays. In the same document, it is indicated that these photostable compositions may additionally contain a UV-blocking inorganic pigment, especially a titanium oxide pigment, which can be coated with a compound, especially a silicone-containing compound. However, this document neither describes nor teaches that, by using a titanium oxide pigment treated with a silicone, it is possible to obtain a reduction in the yellowing effect, as is an object of the present invention.

Thus, in accordance with one of the subjects of the present invention, new cosmetic compositions, especially antisun compositions, are now proposed of the type comprising, in a cosmetically acceptable vehicle, at least one dibenzoylmethane derivative and at least one titanium oxide pigment, which compositions are essentially characterized in that the said titanium oxide pigment is coated and/or treated with a silicone, these compositions being, moreover, devoid of compounds of the benzylidenecamphor type, of the following general formula:

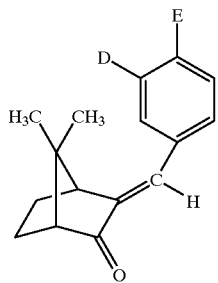

in which D and E are radicals chosen independently from the group consisting of hydrogen, linear or branched $C_1$–$C_{20}$ alkyl radicals and the radical OR in which R is hydrogen or a linear or branched $C_1$–$C_{20}$ alkyl radical.

As indicated previously, the compositions according to the invention have the advantage of being subject to only a very small extent to the phenomenon of yellowing which is customarily caused by the combination of a dibenzoyl-methane derivative with $TiO_2$ pigments.

The present invention also relates to the use of such compositions as, or for the preparation of, cosmetic compositions intended for the protection of the skin and/or hair against ultraviolet radiation, especially solar radiation.

Yet another subject of the present invention is a method of cosmetic treatment for the protection of the skin and/or hair against ultraviolet radiation, especially solar radiation, which essentially consists in applying to the skin and/or hair an effective quantity of a composition according to the invention.

A further subject of the present invention is the use of at least one titanium oxide (nano)pigment, coated and/or treated with a silicone, in antisun compositions containing a dibenzoylmethane derivative, with the aim of simultaneously improving the photoprotective power and the yellowing resistance of the said compositions.

Other characteristics, aspects and advantages of the present invention will appear on reading the detailed description which follows.

As indicated above, the dibenzoylmethane derivatives used in the context of the present invention are products which are already well known per se and are described, in particular, in the abovementioned documents FR-A-2 326 405, FR-A-2 440 933 and EP-A-0 114 607, the teaching of which documents, where it touches on the actual definition of these products, is included in its entirety by way of reference in the present description.

In particular, the dibenzoylmethane derivatives which can be used according to the present invention can be chosen from those corresponding to the following formula:

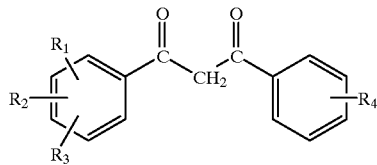

in which $R_1$, $R_2$, $R_3$ and $R_4$, which are identical or different, represent hydrogen or a linear or branched $C_1$–$C_8$ alkyl radical or a linear or branched $C_1$–$C_8$ alkoxy radical.

According to the present invention it is of course possible to employ one or more dibenzoylmethane derivatives.

Among the dibenzoylmethane derivatives to which the present invention relates more particularly, particular mention may be made, without limitation, of:

2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4-methoxy-4'-tert-butyldibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane.

Among the abovementioned dibenzoylmethane derivatives, very particular preference is given, in accordance with the present invention, to the use of 4-methoxy-4'-tert-butyldibenzoylmethane, especially that offered for sale under the trade name "PARSOL 1789" by the company Givaudan, this screening agent thus corresponding to the formula shown below:

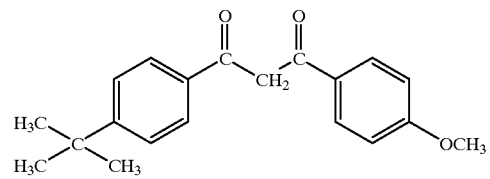

Another dibenzoylmethane derivative which is preferred in accordance with the present invention is 4-isopropyldibenzoylmethane, a screening agent which is sold under the name "EUSOLEX 8020" by the company Merck, which corresponds to the formula shown below:

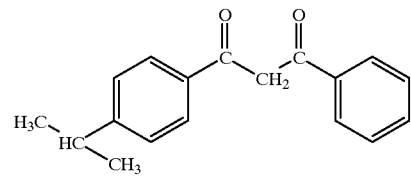

The dibenzoylmethane derivative or derivatives can be present in the compositions according to the invention in amounts which are generally between 0.1 and 10% by weight, preferably in amounts between 0.3% and 5% by weight, relative to the total weight of the composition.

The compositions according to the invention additionally contain inorganic pigments of titanium oxide. Such pigments likewise comprise nanopigments.

The term nanopigment refers to a pigment for which the mean size of the primary particles is chosen from 5 to 100 nm. According to a preferred embodiment of the invention, this size is less than 50 nm.

The titanium oxide can be present in rutile, anatase or amorphous form, but is preferably in rutile and/or anatase form.

According to an essential feature of the present invention, the (nano)pigments which must be used are titanium oxide (nano)pigments treated with a silicone.

In a known manner, the silicones are organosilicon oligomers or polymers with a linear or cyclic, branched or crosslinked structure, of variable molecular weight, which are obtained by polymerization and/or polycondensation of suitably functionalized silanes, and which essentially consist of a repeating sequence of principle units in which the silicon atoms are linked to one another by oxygen atoms (siloxane bond), optionally substituted hydrocarbon radicals being linked directly via a carbon atom to the said silicon atoms. The most common hydrocarbon radicals are the alkyl radicals and, in particular, methyl, fluoroalkyl radicals, aryl radicals, especially phenyl, and alkenyl radicals, especially vinyl; other types of radicals, which can be linked either directly or via a hydrocarbon radical to the siloxane chain are, in particular, hydrogen, halogens and, especially, chlorine, bromine or fluorine, thiols, alkoxy radicals, polyoxyalkylene (or polyether) radicals, and, in particular, polyoxyethylene and/or polyoxypropylene radicals, hydroxyl or hydroxyalkyl radicals, substituted or unsubstituted amine groups, amide groups, acyloxy or acyloxyalkyl radicals, hydroxyalkylamino or aminoalkyl radicals, quaternary ammonium groups, amphoteric or betaine groups, and anionic groups such as carboxylates, thioglycolates, sulphosuccinates, thiosulphates, phosphates and sulphates, this list of course not being in any way limitative (so-called organo-modified silicones).

In the context of the present invention, the term silicones is intended to embrace likewise the silanes which are necessary for their preparation, especially alkylsilanes.

The silicones used for coating pigments suitable for the present invention are preferably chosen from the group consisting of alkylsilanes, polydialkylsiloxanes and polyalkylhydridosiloxanes. Even more preferably, the silicones are chosen from the group consisting of octyltrimethylsilane, polydimethylsiloxanes and polymethylhydridosiloxanes.

Before their treatment with silicones, the $TiO_2$ pigments can of course have been treated with other surface agents, in particular with alumina, silica, aluminium compounds, silicon compounds, or mixtures thereof.

The pigments used in the context of the present invention can be prepared according to surface treatment techniques of a chemical, electronic, mechanochemical and/or mechanical type which are well known to the person skilled in the art and are described, for example, in Cosmetics & Toiletries, February 1990, Vol. 105, pp. 53–64. It is also possible to use commercial products.

The titanium oxide nanopigments which are particularly well-suited to carrying out the present invention are preferably $TiO_2$ which is treated with octyltrimethylsilane and for which the mean size of the primary particles is between 25 and 40 nm, such as that sold under the trade name "T 805" by the company Degussa Silices, alumina-coated $TiO_2$ which is treated with a polydimethylsiloxane and for which the mean size of the primary particles is 20 nm, such as that sold under the trade name "UV Titan M 262" by the company Kemira, $TiO_2$ treated with a polydimethylsiloxane, and for which the mean size of the primary particles is 21 nm, such as that sold under the trade name "70250 Cardre UF $TiO_2$ S13" by the company Cardre, anatase/rutile $TiO_2$ treated with a polymethylhydridosiloxane, and for which the mean size of the primary particles is 25 nm, such as that sold under the trade name "Micro Titanium dioxide USP grade hydrophobic" by the company Color Techniques, and the silica/alumina-coated $TiO_2$ which is treated with a silicone and for which the mean size of the primary particles is 15 nm, such as that sold under the trade name "MT-100 SAS" by the company Tayca.

The (nano)pigments can be present in the compositions according to the invention in amounts which are generally between 0.1 and 30% by weight, and preferably in amounts of between 0.5% and 20% by weight relative to the total weight of the composition.

The antisun cosmetic compositions according to the invention can of course contain one or more additional hydrophilic or lipophilic sunscreens which are active in UVA and/or UVB (absorbers) and which are different, of course, from the dibenzoylmethane derivatives mentioned above. These additional screening agents can be chosen in particular from cinnamic derivatives, salicylic derivatives, camphor derivatives, triazine derivatives, benzophenone derivatives, β,β-diphenylacrylate derivatives, p-aminobenzoic acid derivatives, and the polymer screening agents and silicone screening agents described in the Application WO-93/04665. Other examples of organic screening agents are given in the Patent Application EP-A 0 487 404.

The compositions according to the invention can also contain tanning agents and/or artificial tanning agents for the skin (self-tanning agents) such as, for example, dihydroxyacetone (DHA).

The compositions of the invention may additionally comprise conventional cosmetic adjuvants which are chosen in particular from fats, organic solvents, ionic or nonionic thickeners, demulcents, antioxidants, opacifying agents, stabilizers, emollients, silicones, α-hydroxy acids, antifoams, moisturizers, vitamins, fragrances, preservatives, surfactants, fillers, polymers, propellants, alkalifying or acidifying agents, colourants, or any other ingredient which is commonly used in cosmetics, especially for the manufacture of antisun compositions in the form of emulsions.

The fats may consist of an oil or a wax or mixtures thereof, and they also comprise fatty acids, fatty alcohols and fatty acid esters. The oils can be chosen from animal, vegetable, mineral or synthetic oils and, in particular, from liquid petroleum, paraffin oil, volatile or nonvolatile silicone oils, isoparaffins, poly-α-olefins and fluorinated and perfluorinated oils. Similarly, the waxes can be chosen from animal, fossil, vegetable, mineral or synthetic waxes which are known per se.

The organic solvents which may be mentioned include lower polyols and alcohols.

The thickeners can be chosen in particular from crosslinked polyacrylic acids, modified or unmodified guar gums and celluloses, such as hydroxypropyl guar gum, methylhydroxyethylcellulose, hydroxypropylmethylcellulose or else hydroxyethylcellulose.

The person skilled in the art will of course ensure that any optional additional compounds and/or their quantities are chosen such that the advantageous properties, and especially that of a reduction in the phenomenon of yellowing, which are attached intrinsically to the combination according to the invention are not, or not substantially, impaired by the addition or additions which are envisaged.

The compositions of the invention can be prepared in accordance with techniques which are well known to the person skilled in the art, especially those intended for the preparation of oil-in-water or water-in-oil emulsions.

These compositions can be provided, in particular, in the form of simple or complex emulsions (O/W, W/O, O/W/O or W/O/W) such as creams, milks, gels or cream gels, powders or solid sticks and, if appropriate, may be packaged as aerosols and provided in the form of mousses or sprays. These compositions are preferably provided in the form of an O/W emulsion.

The cosmetic compositions of the invention can be used as compositions for protecting human skin or hair against ultraviolet radiation, as antisun compositions or as make-up products.

When the cosmetic composition according to the invention is used for the protection of the human skin against UV rays, or as an antisun composition, it can be provided in the form of a suspension or dispersion in solvents or fats, in the form of a nonionic vesicle dispersion or else in the form of an emulsion, preferably of the oil-in-water type, such as a cream or a milk, or in the form of an ointment, gel, cream gel, solid stick, aerosol mousse or spray.

When the cosmetic composition according to the invention is used for the protection of hair, it can be provided in the form of a shampoo, lotion, gel, emulsion, nonionic vesicle dispersion or hair lacquer and may constitute, for example, a rinsing composition to be applied before or after shampooing, before or after dyeing or bleaching, before, during or after a permanent-waving or hair-straightening operation, as a treatment or styling lotion or gel, as a lotion or gel for blow-drying or setting, or a composition for the permanent waving or straightening, dyeing or bleaching of hair.

When the composition is used as a make-up product for the eyelashes, eyebrows or skin, such as a skin treatment cream, a foundation, a lipstick, an eye shadow, a blusher, a mascara or an eye-liner, it can be provided in solid or pastelike form, in an anhydrous or aqueous form, such as oil-in-water or water-in-oil emulsions, nonionic vesicle dispersions or else suspensions.

By way of indication, for the antisun formulations according to the invention which have a vehicle of the oil-in-water emulsion type, the aqueous phase (comprising in particular the hydrophilic screening agents) generally represents from 50 to 95% by weight, preferably from 70 to 90% by weight, relative to the overall formulation, the oily phase (comprising in particular the lipophilic screening agents) represents from 5 to 50% by weight, preferably from 10 to 30% by weight, relative to the overall formulation, and the (co)emulsifier(s) represent(s) from 0.5 to 20% by weight, preferably from 2 to 10% by weight, relative to the overall formulation.

As indicated at the beginning of the description, a further subject of the present invention is a method for cosmetic treatment of the skin or hair which is intended to protect them against the effects of UV rays, and which consists in applying to them an effective quantity of a cosmetic composition as defined above.

Concrete examples will now be given which illustrate the invention but are in no way limitative.

EXAMPLE 1

Comparative tests were carried out in order to demonstrate the improvement provided by the use of a titanium oxide nanopigment coated with a silicone in 4-methoxy-4'-tert-butyldibenzoylmethane/titanium oxide nanopigment combinations.

For this purpose ten dispersions were produced each containing, in an identical vehicle ($C_{12}$–$C_{15}$ alkyl benzoate), 4-methoxy-4'-tert-butyldibenzoylmethane in combination with a titanium oxide nanopigment, and varying the nature of the titanium oxide nanopigment; for dispersions 1, 2 and 3, the pigments used are conventional (uncoated) titanium oxide nanopigments; for dispersions 4 and 5, the pigments used are titanium oxide nanopigments coated with compounds other than a silicone; and for dispersions 6, 7, 8, 9 and 10, the pigments used are titanium oxide nanopigments coated with a silicone, in accordance with the present invention.

In order to measure the change in colour caused by the presence of 4-methoxy-4'-tert-butyldibenzoylmethane in combination with a titanium oxide nanopigment in the dispersion, for each of these dispersions 1 to 10 a standard dispersion was produced which did not contain 4-methoxy-4'-tert-butyldibenzoylmethane but did contain, in the same vehicle, the nanopigment of the dispersion 1 to 10 which it is desired to test.

The various dispersions were produced as follows:
Dispersions 1 to 10

18 g of a mixture formed from 16 g of $C_{12}$–$C_{15}$ alkyl benzoate sold under the trade name "Finsolv TN" by Finetex and from 2 g of 4-methoxy-4'-tert-butyldibenzoylmethane sold under the trade name "Parsol 1789" by Givaudan, which mixture was homogenized beforehand at 80° C., were added in a flask to 2 g of titanium oxide nanopigment. The flask was then shaken in order to homogenize the dispersion.
Standard dispersions These were produced in accordance with the same procedure as for dispersions 1 to 10, using 18 g of $C_{12}$–$C_{15}$ alkyl benzoate (no "Parsol 1789").

Dispersions 1 to 10 were subsequently stored away from light for 24 h. The calorimetric measurements were made using a Minolta CM 1000 calorimeter. A sample of each rehomogenized dispersion was analysed. For each sample, the values of L*, a* and b* (where L represents luminance, a represents the red-green axis (−a=green, +a=red) and b represents the yellow-blue axis (−b=blue, +b=yellow)) were measured and the colour change ΔE* was calculated from the changes ΔL*, Δa* and Δb* between the dispersion 1 to 10 to be tested and its standard dispersion, in accordance with the following equation:

$$\Delta E^* = \sqrt{(\Delta L^*)^2 + (\Delta a^*)^2 + (\Delta b^*)^2}$$

The smaller ΔE*, the greater the reduction n colour change.

The compositions of dispersions 1 to 10 and he results obtained are set out in the following table (I):

TABLE I

| Dispersion | Nanopigment | ΔE* |
|---|---|---|
| 1 Comparative | 30 nm anatase $TiO_2$ sold under the name "Transparent PW" by Les colorants Wackherr | 19 |
| 2 Comparative | 35 nm $TiO_2$ sold under the name "MT 500 B" by Tayca | 12 |
| 3 Comparative | 70 nm rutile $TiO_2$ sold under the name "MT-Trial product No. 482" by Tayca | 10 |
| 4 Comparative | 15 nm rutile $TiO_2$ coated with alumina/silica and sold under the name "MT 100 SA" by Tayca | 12 |
| 5 Comparative | 15 nm rutile $TiO_2$ coated with alumina hydroxide/stearic acid and sold under the name "MT 100 T" by Tayca | 9 |
| 6 Invention | 25–40 nm $TiO_2$ treated with octyltrimethylsilane and sold under the name "T 805" by Degussa | 6 |
| 7 Invention | 20 nm $TiO_2$ coated with alumina treated with polydimethylsiloxane and sold under the name "UV Titan M 262" by Kemira | 4 |
| 8 Invention | 21 nm $TiO_2$ treated with polydimethylsiloxane and sold under the name "70250 Cardre UF $TiO_2$ S13" by Cardre | 4 |
| 9 Invention | 25 nm rutile/anatase $TiO_2$ treated with polymethylhydridosiloxane and sold under the name "Micro Titanium dioxide USP grade hydrophobic" by Color Techniques | 3 |
| 10 Invention | 15 nm $TiO_2$ coated with silica/alumina treated with silicone and sold under the name "MT 100 SAS" by Tayca | 3 |

These results clearly show that the coating of the titanium oxide nanopigment with a silicone, whether this nanopigment is already coated with other chemical compounds (as in the case of dispersions 7 and 10) or not (dispersions 6, 8 and 9), significantly reduces the colour change, and in particular the yellowing, owing to the combination of 4-methoxy-4'-tert-butyldibenzoylmethane and titanium oxide nanopigment relative to the dispersions containing uncoated titanium oxide nanopigments (dispersions 1, 2 and 3) or titanium oxide nanopigments whose coating contains no silicone (dispersions 4 and 5).

EXAMPLE 2

The following composition gives a concrete example of a high-protection sun formula in accordance with the invention, in the form of an O/W emulsion. The quantities are expressed in % by weight relative to the total weight of the composition:

Phase A

| | |
|---|---|
| 4-methoxy-4'-tert-butyldibenzoylmethane sold under the trade name "Parsol 1789" by Givaudan | 3% |
| $C_{12}$–$C_{15}$ alkyl benzoate sold under the trade name "Finsolv TN" by Finetex | 2% |
| cetyl alcohol sold under the trade name "Lanette 16 NF" by Henkel | 1.5% |
| dimethicone sold under the trade name "DC 200 Fluid" by Dow Corning | 0.5% |
| octocrylene sold under the trade name "Uvinul N 539" by BASF | 10% |
| mixture of PEG 100 stearate and glyceryl stearate, sold under the trade name "Arlacel 165" by ICI | 1.5% |
| TiO$_2$ treated with alkylsilane and sold under the trade name "T 805" by Degussa Silices | 5% |

Phase B

| | |
|---|---|
| glycerol | 7% |
| carbomer sold under the trade name "Carbopol 980" by Goodrich | 0.2% |
| disodium EDTA sold under the trade name "Edeta BD" by BASF | 0.1% |
| water | qs 100% |

Phase C

| | |
|---|---|
| cyclomethicone sold under the trade name "DC 245 Fluid" by Dow Corning | 10% |
| Preservatives | qs |
| Neutralizing agent | qs pH = 7 |

Procedure: The above emulsion was produced as follows: phase A was heated to 80° C. in order to melt all of the constituents. Phase B was also heated to 80° C. after having dispersed the carbomer therein beforehand. Phase A was then poured into phase B while hot, at about 65° C. The mixture was stirred for 10 minutes for emulsification. Phase C was then added with stirring, after which the carbomer was neutralized. Finally, the emulsion was terminated by stirring until complete cooling was obtained (≈20–25° C.).

What is claimed is:

1. A cosmetic composition suitable for topical application to the skin or hair which comprises in a cosmetically acceptable carrier, a combination of at least one dibenzoylmethane derivative and at least one titanium dioxide pigment, wherein said composition provokes a yellowing effect, and wherein said titanium dioxide pigment is coated and/or surface-treated with a silicone selected from the group consisting of an octyltrimethylsilane, polydimethylsiloxane, and polymethylhydridosiloxane, and wherein said composition is devoid of benzylidene camphor compounds having the generic structure

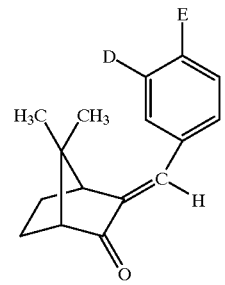

wherein D and E are radicals selected from the group consisting of hydrogen, linear or branched $C_1$–$C_{20}$ alkyl radicals, and the radical OR wherein R is hydrogen or a linear or branched $C_1$–$C_{20}$ alkyl radical, and wherein said composition possesses and enhanced photoprotective power and reduced yellowing effect relative to a cosmetic composition which comprises an uncoated titanium dioxide pigment.

2. A composition according to claim 1, wherein said dibenzoylmethane compound is selected from compounds having the generic formula

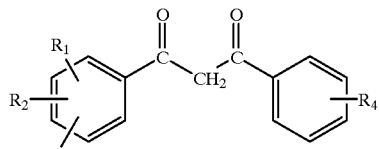

in which $R_1$, $R_2$, $R_3$ and $R_4$, which are identical or different, represent hydrogen or a linear or branched $C_1$–$C_8$ alkyl radical or a linear or branched $C_1$–$C_8$ alkoxy radical.

3. A composition according to claim 1, wherein the dibenzoyl compound is selected from the groups consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-methoxy-4'-tert-butyldibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane.

4. The composition according to claim 3, wherein said dibenzoyl compound is 4-methoxy-4'-tert-butyldibenzoylmethane.

5. The composition according to claim 3, wherein said dibenzoylmethane compound is 4-isopropyldibenzoylmethane.

6. The composition according to claim 1, wherein said pigment prior to treatment or coating with said silicone is coated with a different coating agent than said recited silicones.

7. The composition according to claim 6, wherein said other coating agent is selected from the group consisting of alumina, silica, aluminum compounds, silicon compounds, and mixtures thereof.

8. The composition according to claim 1, wherein the mean size of the primary particles of said titanium dioxide pigment range from 5 to 100 nm.

9. The composition according to claim 8, wherein the mean size of said primary particles is less than 50 nm.

10. A composition according to claim 1, wherein said pigment is a titanium dioxide treated with octyltrimethylsilane.

11. A composition according to claim 1, wherein said pigment is a titanium dioxide coated with alumina and surface treated with a polydimethylsiloxane.

12. A composition according to claim 1, wherein said titanium dioxide pigment is a titanium dioxide treated with a polydimethylsiloxane.

13. A composition according to claim 1, wherein said titanium dioxide pigment is an anatase/rutile titanium dioxide treated with a polymethylhydridosiloxane.

14. A composition according to claim 1, wherein said dibenzoylmethane compound is present in an amount ranging from 0.1 to 10% by weight relative to the total weight of said composition.

15. A composition according to claim 14, wherein said dibenzoyl compound is present in an amount ranging from 0.3 to 5% by weight relative to the total weight of the composition.

16. A composition according to claim 1, wherein the amount of said pigment ranges from 0.1 to 30% by weight relative to the total weight of the composition.

17. A composition according to claim 16, wherein the amount of said pigment ranges from 0.5 to 20% by weight relative to the total weight of the composition.

18. A method of cosmetic treatment which provides for protection of the skin and/or hair against ultraviolet radiation which comprises applying to the skin and/or hair an amount of a cosmetic composition according to claim 1 sufficient to protect said skin and or hair against ultraviolet radiation.

19. A method according to claim 18, wherein said dibenzoylmethane compound is a compound having the generic formula:

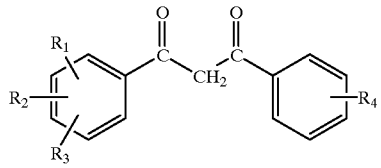

in which $R_1$, $R_2$, $R_3$ and $R_4$, which are identical or different, represent hydrogen or a linear or branched $C_1$–$C_8$ alkyl radical or a linear or branched $C_1$–$C_8$ alkoxy radical.

20. The method according to claim 19, wherein said dibenzoylmethane compound is selected from the group consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-methoxy-4'-tert-butyldibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane.

21. A method according to claim 20, wherein said dibenzoylmethane compound is 4-methoxy-4'-tert-butyldibenzoylmethane.

22. A method according to claim 20, wherein said dibenzoylmethane compound is 4-isopropyldibenzoylmethane.

23. A method according to claim 19, wherein said titanium dioxide pigment, prior to coating or treatment with said silicone, is coated with a different coating agent than said recited silicones.

24. A method according to claim 23, wherein said different coating agent is selected from the group consisting of alumina, silica, aluminum compounds, silicon compounds, and mixtures thereof.

25. A method according to claim 19, wherein the mean size of the primary particles of said titanium dioxide pigment ranges from 5 to 100 nm.

26. A method according to claim 19, wherein the mean size of the primary particles of said titanium dioxide are less than 50 nm.

27. A method according to claim 19, wherein the pigment is a titanium dioxide treated with octyltrimethylsilane.

28. A method according to claim 19, wherein said titanium dioxide pigment is a titanium dioxide coated with alumina which is treated with a polydimethylsiloxane.

29. A method according to claim 19, wherein said titanium dioxide pigment is a titanium dioxide treated with a polydimethylsiloxane.

30. A method according to claim 19, wherein said titanium dioxide pigment is an anatase/rutile titanium dioxide treated with a polymethylhydridosiloxane.

31. A method according to claim 19, wherein said dibenzoylmethane compound is present in an amount ranging from 0.1 to 10% by weight relative to the total weight of the composition.

32. A method according to claim 31, wherein said dibenzoylmethane compound is present in an amount ranging from 0.3 to 5% by weight relative to the total weight of the composition.

33. A method according to claim 19, wherein said titanium dioxide pigment is present in an amount ranging from 0.1 to 30% by weight relative to the total weight of the composition.

34. A method according to claim 33, wherein said pigment is present in an amount ranging from 0.5 to 20% by weight relative to the total weight of said composition.

* * * * *